United States Patent [19]

Harandi

[11] Patent Number: 4,820,877

[45] Date of Patent: Apr. 11, 1989

[54] ETHERIFICATION PROCESS IMPROVEMENT

[75] Inventor: Mohsen N. Harandi, Lawrenceville, N.J.

[73] Assignee: Mobil Oil Corporation, New York, N.Y.

[21] Appl. No.: 138,745

[22] Filed: Dec. 28, 1987

[51] Int. Cl.$^4$ .................. C07C 41/06; C07C 41/34
[52] U.S. Cl. .................. 568/697; 568/144
[58] Field of Search .................. 568/697, 699

[56] References Cited

U.S. PATENT DOCUMENTS

| | | |
|---|---|---|
| 4,302,298 | 11/1981 | Mikitenko et al. .................. 568/699 |
| 4,440,963 | 4/1984 | Childs .................. 568/699 |
| 4,544,776 | 10/1985 | Osterburg et al. . |
| 4,603,225 | 7/1986 | Colainne et al. . |
| 4,665,237 | 5/1987 | Arakawa et al. . |

Primary Examiner—Howard T. Mars
Attorney, Agent, or Firm—Alexander J. McKillop; Charles J. Speciale; L. G. Wise

[57] ABSTRACT

An improved etherification process is described for the manufacture of methyl tertiary alkyl ethers such as methyl tertiary butyl ether and methyl tertiary amyl ether. In one embodiment etherification is conducted in the presence of a large excess of methanol wherein unreacted methanol is separated in a fractionator utilizing a light hydrocarbon stripping gas to separate the methanol-hydrocarbon azeotrope. In another embodiment unreacted methanol from the etherification reaction is removed by water washing. The aqueous mixture containing unreacted methanol is separated in a stripping zone employing fuel gas as a stripping media.

5 Claims, 3 Drawing Sheets

ETHERIFICATION PROCESS IMPROVEMENT

This invention relates to an improved etherification process for the manufacture of methyl tertiary alkyl ethers. More particularly, the invention relates to improvements in the separation of unreacted methanol from etherification effluent streams thereby enabling the use of large excess amounts of methanol in the etherification reaction.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is a new process to produce high octane gasolines blended with lower aliphatic alkyl ethers as octane boosters and supplementary fuels. $C_5-C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiary-amyl methyl ether (TAME). In these etherification processes, a problem of major importance is the separation of methanol from the etherification reaction product due to the proclivity of methanol to form a very dilute azeotropic mixture with hydrocarbons and the strong solubility of methanol in both water and hydrocarbons. While it would be useful from an equilibrium standpoint to use large excesses of methanol in etherification, subsequent separation problems have limited that process improvement. Due largely to these factors, the cost associated with methanol separation and recycling in the etherification reaction represents approximately 30% of the cost of the total etherification process.

In response to the aforestated problem, it is an object of the instant invention to provide an improvement to the etherification process steps leading to the separation of unreacted methanol.

A further object of the present invention is to improve the separation of unreacted methanol in a manner conducive to the use of increased amounts of excess methanol in the etherification reaction.

A further object of the present invention is to provide an improved process for etherification of $C_4-C_7$ isoolefins with methanol leading to increased yields of methyl tertiary butyl ether (MTBE) and methyl tertiary amyl ether (TAME).

SUMMARY OF THE INVENTION

It has been discovered that the etherification process consisting of the reaction of methanol and $C_4+$ hydrocarbons containing isoolefin to produce methyl tertiary alkyl ethers, such as methyl tertiary butyl ether and methyl tertiary amyl ether, is improved both in terms of product yield and process cost by the use of refinery fuel gas as a stripping medium to separate unreacted methanol from the etherification reaction products. As a result thereof, larger quantities of a stoichiometric excess of methanol can be used in the etherification step which drives the chemical equilibrium of that reaction toward the formation of the desired methyl tertiary alkyl ethers.

In one embodiment fuel gas stripping medium is introduced into the fractionator or debutanizer employed in the initial separation of the etherification reaction effluent stream.

In another embodiment fuel gas is used as the stripping medium to separate methanol from the aqueous stream from a water wash extraction tower. The combination of water wash extraction of methanol and fuel gas stripping of the aqueous methanol stream can be incorporated in the overall etherification process upstream or downstream of the main product fractionator or debutanizer.

More specifically, the invention consists of an improved etherification process for the production of methyl tertiary alkyl ethers, comprising the steps of:

(a) contacting a methanol feedstream and a $C_4+$ hydrocarbon feedstream with an acid etherification catalyst in an etherification zone under etherification conditions whereby an effluent stream is produced comprising methyl tertiary alkyl ethers, unreacted methanol and $C_4+$ hydrocarbons;

(b) passing said effluent stream to a fractionator for separation in contact with light hydrocarbon stripping gas;

(c) recovering an overhead stream from said fractionator comprising methanol, stripping gas and $C_4$'s and a bottom fractionator stream comprising $C_5+$ ethers.

DETAILED DESCRIPTION OF THE INVENTION

Figure 1:
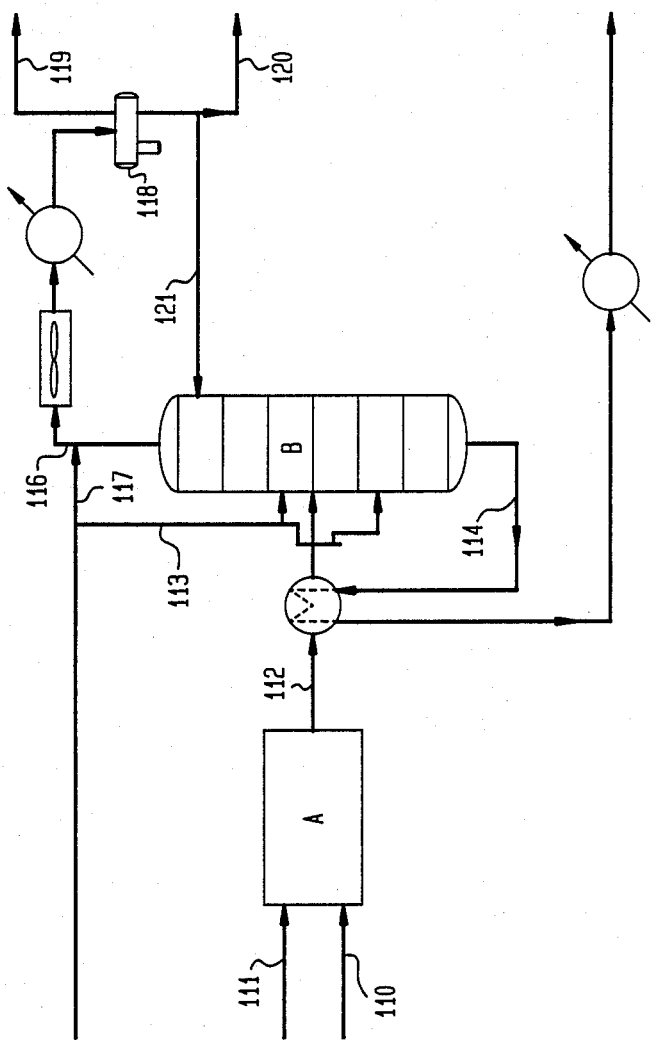
FIG. 1 is a schematic drawing of the flowchart of the present invention using fuel gas as a stripping medium in the etherification effluent stream main fractionator.

In the preferred embodiments of this invention, methanol is reacted with hydrocarbon feedstock containing olefins, particularly iso-olefins, to produce methyl tertiary alkyl ethers, particularly methyl tertiary butyl ether and methyl tertiary amyl ether. In the etherification reaction, methanol is generally present in an excess amount between 2 wt. % to 100 wt %, based upon iso-olefins. Excess methanol means excess methanol above the stoichiometric equivalent amount to convert isoolefins in the hydrocarbon feedstream to methyl tertiary alkyl ethers. Following the etherification reaction, the etherification reaction effluent stream, which comprises unreacted methanol, hydrocarbons including a major portion of $C_4+$ hydrocarbons and methyl tertiary alkyl ethers, are separated according to the novel separation steps of the instant invention employing fuel gas stripping or water washing in conjunction with fuel gas stripping.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The reaction of methanol with isobutylene and isoamylenes at moderate conditions with a resin catalyst is known technology, as provided by R. W. Reynolds, et al., *The Oil and Gas Journal,* June 16, 1975, and S. Pecci and T. Floris, *Hydrocarbon Processing,* Dec. 1977. An article entitled "MTBE and TAME—A Good Octane Boosting Combo," by J. D. Chase, et al., *The Oil and Gas Journal,* Apr. 9, 1979, pages 149-152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J. D. Chase, et al., *Oil and Gas Journal,* Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$-$C_7$ isoolefins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

Referring now to FIG. 1, a schematic process flow diagram is presented for a specific embodiment of the instant invention for the elimination or separation of methanol-hydrocarbon azeotrope from an etherification reaction. In this embodiment and subsequent embodiments of the present invention fuel gas is used as a stripping medium to accomplish the separation of methanol. Fuel gas, as employed herein, refers to refinery fuel gas which generally constitutes a combination of by-product gaseous streams from refinery operations rich in light hydrocarbons. Preferably, the fuel gas source is the FCC fuel gas and/or FCC $C_3$ stream. The composition of a typical FCC fuel gas is as follows:

| Component Gas | Volume Percent |
|---|---|
| Hydrogen | 7.8 |
| Methane | 38.2 |
| Nitrogen | 7.2 |
| Carbon dioxide | 1.4 |
| Ethylene | 17 |
| Ethane | 17.4 |
| Propylene | 3.2 |
| Propane | 1 |
| $C_4+$ | 6.2 |
| water | 0.4 |

In FIG. 1, a methanol feedstream 110 and a $C_4+$ hydrocarbon feedstream 111 are passed to an etherification reaction unit A for etherification in the presence of an acid catalyst according to known procedures. As previously noted the hydrocarbon stream is rich in iso-olefins and methanol is present in a large excess, based upon those iso-olefins. In known etherification processes, etherification can be conducted generally with an excess methanol of about 3%. In the process according to the present invention methanol can be present in an amount between 2 and 100 wt. %, but preferably about 50 wt. %. The etherification effluent stream 112 comprises $C_5+$ methyl tertiary alkyl ethers, particularly methyl tertiary butyl ether and methyl tertiary amyl ether. Effluent stream 112 is passed to a mid-portion of a product fractionator B such as a debutanizer which generally consists of about 20 to 35 stages. A fuel gas stream 113 is introduced into the product fractionator as a stripping medium preferably at a position above the feedstream 112 although the stripping gas may be introduced below feedstream 112. From fractionator B bottom stream 114 is separated which comprises $C_5+$ ethers, particularly methyl tertiary butyl ether and methyl tertiary amyl ether. Stream 114 may be optionally employed in indirect heat transfer with etherification reactor effluent 112. The overhead stream 116 from fractionator B comprises a liquid and vapor stream that includes excess or unreacted methanol, fuel gas and $C_4$ hydrocarbons. Optionally, fuel gas may be introduced to the overhead stream through conduit 117. The overhead stream is cooled and separated into liquid and vapor fractions in separator 118. The vapor fraction contains methanol and fuel gas 119 while the liquid fraction 120 comprises primarily $C_4$s a portion of which are passed as a reflux stream to the product fractionator through conduit 121. Depending on the process application, the $C_4$ product can be sent with the light components to the vapor overhead stream 119.

Figure 2:
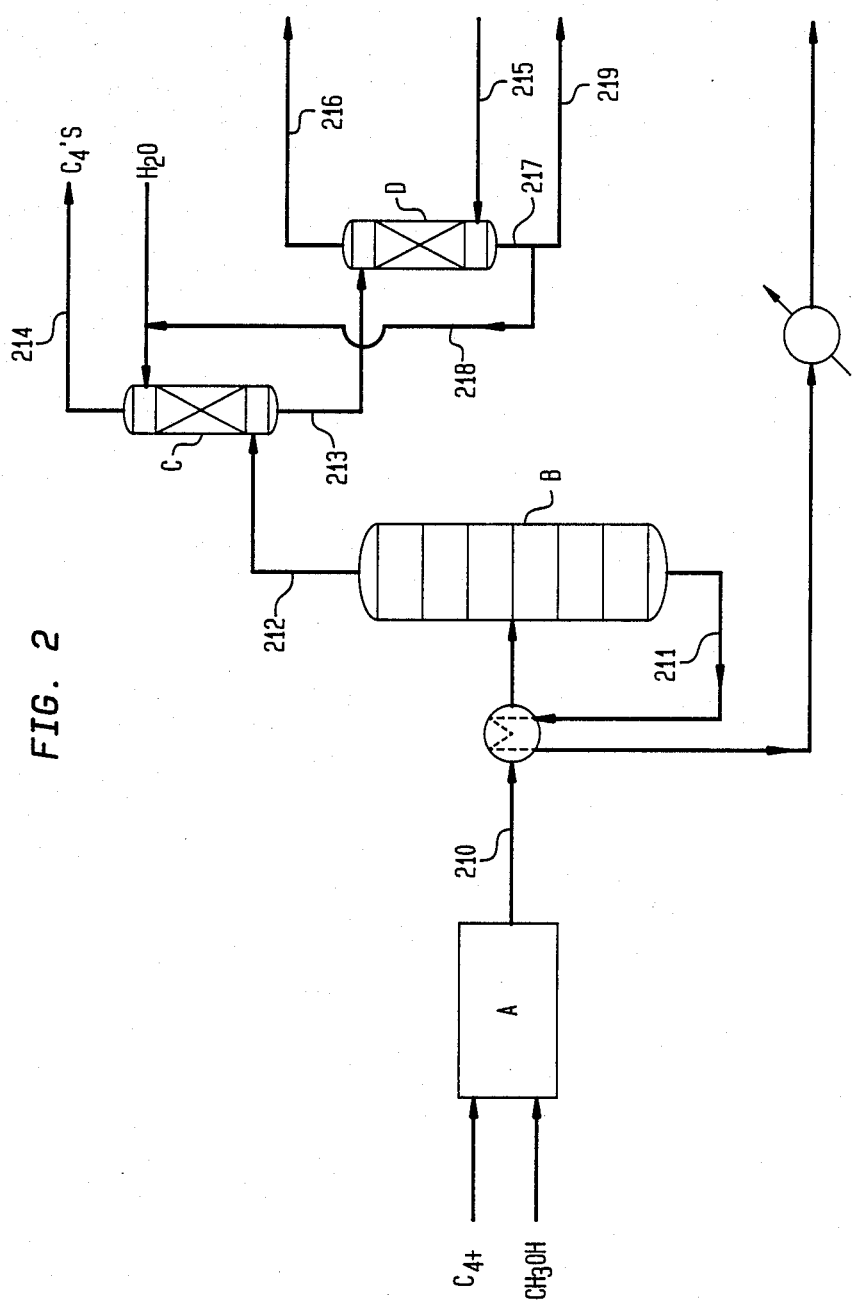
FIG. 2 is a schematic flow diagram of an embodiment of the present invention employing downstream water wash followed by fuel gas methanol stripping from the main fractionator overhead stream.

Referring now to FIG. 2 another embodiment of the present invention utilizing fuel gas to strip unreacted methanol from an etherification reaction is presented. From the etherification reaction section A an effluent stream 210 comprising excess or unreacted methanol, $C_5+$ ethers, and unreacted $C_4+$ hydrocarbons is passed to product fractionator B. The product ethers are separated as a bottom stream 211 and comprise a major portion of methyl tertiary butyl ether and methyl tertiary amyl ether. The fractionator overhead stream 212 which comprises unreacted methanol as a mixture with hydrocarbon is passed to water wash tower C wherein methanol is separated as a bottom aqueous stream 213 and the hydrocarbon portion of overhead stream 212 is separated as an overhead stream 214 from the water wash tower and includes primarily $C_4$ hydrocarbons. The aqueous methanol stream 213 is passed to a top portion of stripping tower D and is stripped using fuel gas stripping media, preferably a fuel gas stream which is saturated with water, introduced to a bottom portion of the tower through conduit 215. The overhead from the stripping tower 216 comprises fuel gas containing methanol stripped from the aqueous methanol stream. Waste water from the stripping operation is removed from the bottom portion of stripping tower D through conduit 217. A portion of the waste water is recycled to the wash tower via conduit 218 while the balance of the waste water is discharged through conduit 219. In the design according to the present invention, unlike conventional designs, almost no energy loss is associated with methanol recovery from the etherification debutanizer overhead. In many cases, no heating and cooling is required in the water wash fuel gas stripping section.

Figure 3:
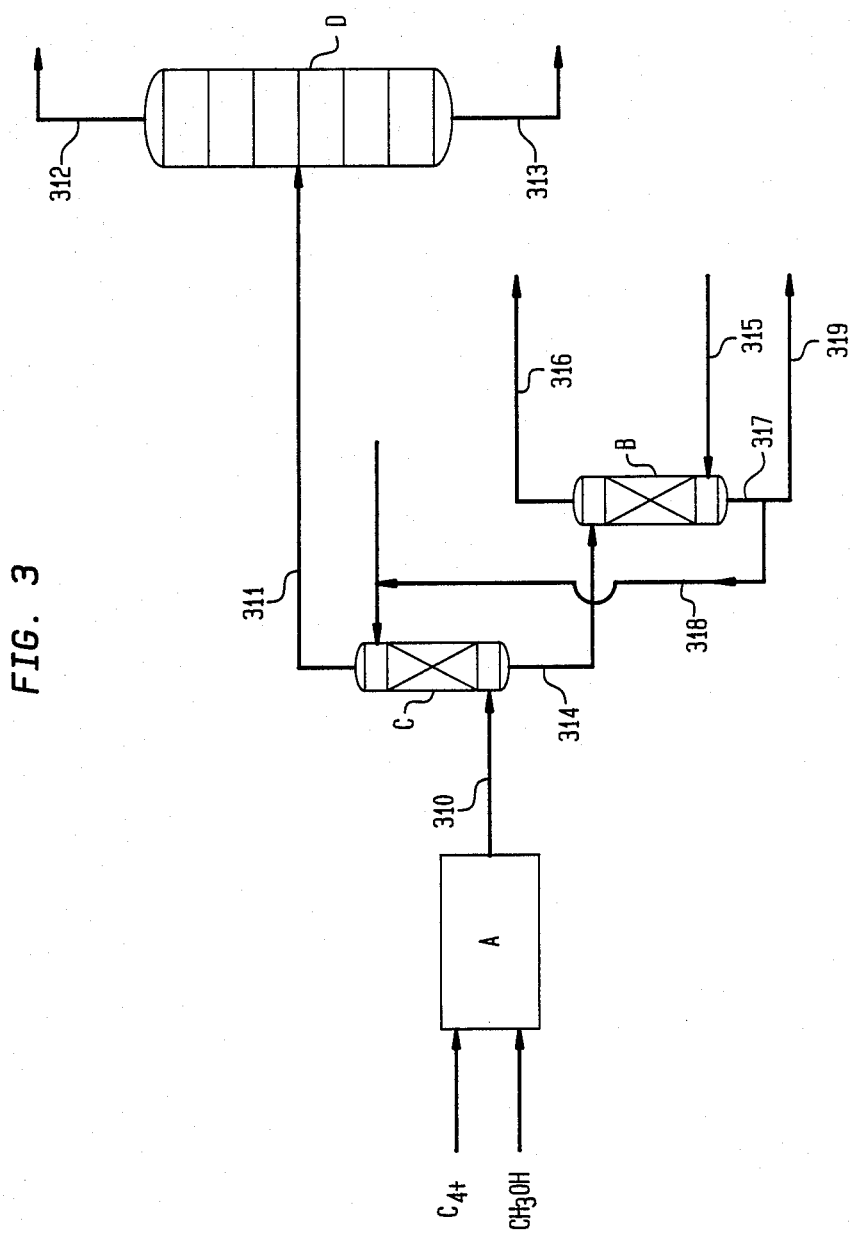
FIG. 3 is a schematic diagram of water washing and methanol stripping using fuel gas as stripping medium upstream of the main product fractionator.

An alternative to the embodiment of the present invention presented in FIG. 2 is illustrated as a schematic diagram in FIG. 3. In FIG. 3 the etherification reactor A effluent stream 310 is first passed to a bottom portion of water wash tower C. The overhead stream 311 from the water wash tower comprises $C_5+$ ethers and unreacted hydrocarbon which are passed to fractionator D for separation into overhead stream 312 containing $C_4$ hydrocarbons and a bottom stream 313 containing $C_5+$ ethers, including methyl tertiary butyl ether and methyl tertiary amyl ether. From water wash tower C a bottom stream 314 is passed to stripper B wherein the aqueous methanol stream 314 is stripped of methanol using fuel gas stripping media introduced to the stripper through conduit 315. The overhead stream 316 from the stripper comprises unreacted methanol from the etherification reaction and fuel gas. Waste water is withdrawn as a bottom stream 317, a portion of which is passed through conduit 318 to the water wash tower.

While the invention has been described by specific examples in embodiments, there is no intent to limit the inventive concept except as set forth in the following claims:

What is claimed is:

1. In a process for the manufacture of methyl tertiary butyl ether comprising contacting a methanol feedstream containing a stoichiometric excess of methanol based on iso-olefins and a $C_4+$ hydrocarbon feedstream rich in isobutylene with an acidic etherification catalyst in an etherification zone under etherification conditions; passing said etherification zone effluent stream to a fractionator for separation; recovering a fractionator bottom stream containing methyl tertiary butyl ether and an overhead fraction containing unreacted methanol and hydrocarbon azeotrope, the improvement comprising: contacting said $C_4+$ hydrocarbon feedstream with a stoichiometric excess of methanol based on iso-olefins of between 3% and 100% whereby conversion of isobutylene is increased to produce methyl tertiary butyl ether; passing a refinery fuel gas into a mid-portion of said fractionator to enhance the separation of unreacted methanol into the overhead stream containing $C_4$ hydrocarbons; and cooling said overhead stream to separate vapor containing methanol and said fuel gas and liquid containing $C_4$ hydrocarbons.

2. The process of claim 1 wherein said fuel gas comprises FCC fuel gas.

3. The process of claim 1 wherein said stoichiometric excess is between about 5–20%.

4. In a process for the manufacture of methyl tertiary butyl ether comprising contacting a methanol feedstream containing up to a 3% stoichiometric excess of methanol based on iso-olefins and a $C_4+$ hydrocarbon feedstream rich in isobutylene with an acidic etherification catalyst in an etherification zone under etherification conditions; passing said etherification zone effluent stream to a fractionator for separation; recovering a fractionator bottom stream containing methyl tertiary butyl ether and an overhead fraction containing unreacted methanol and hydrocarbon azeotrope, the improvement comprising: separating said overhead stream in a water wash extraction tower into an overhead stream comprising $C_4$ hydrocarbons and a bottom stream comprising aqueous unreacted methanol; and contacting said aqueous methanol with refinery fuel gas in a stripping zone whereby methanol is separated from unreacted aqueous methanol.

5. The process of claim 4 wherein said fuel gas comprises FCC fuel gas.

* * * * *